Figure 1:
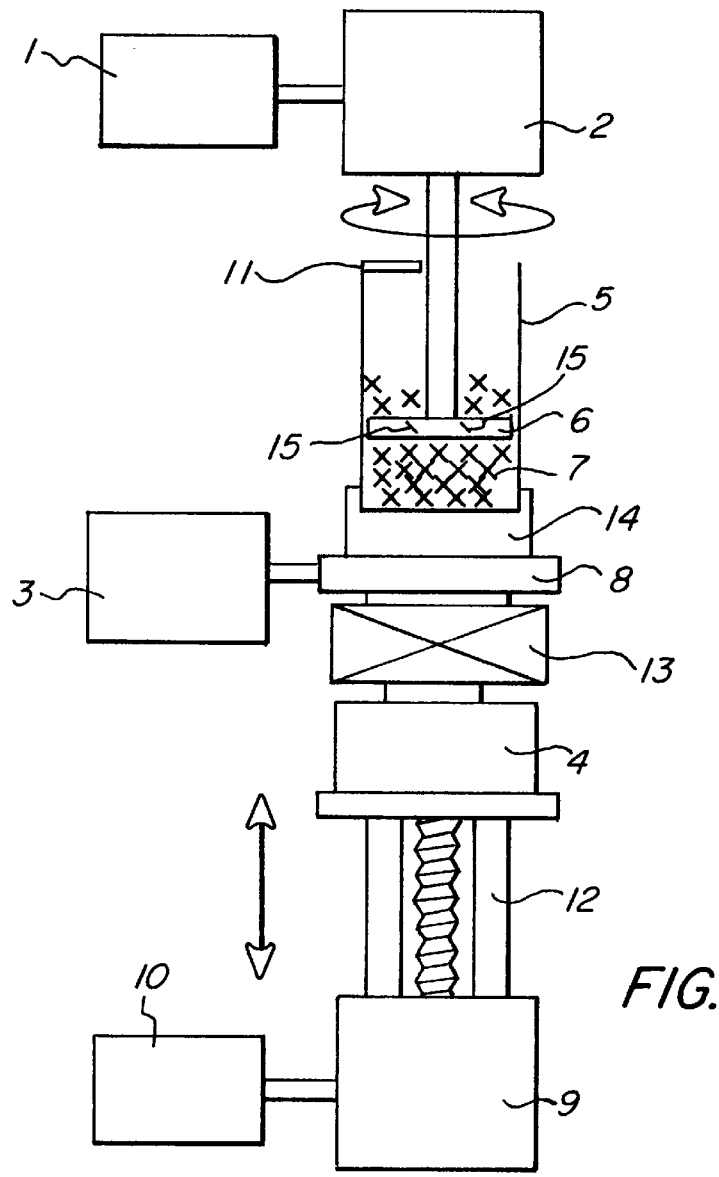
Figure 2A:
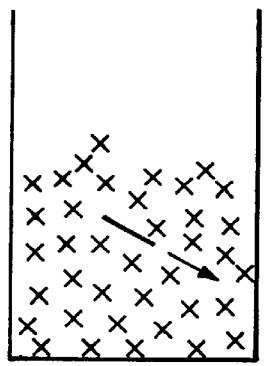
Figure 2B:
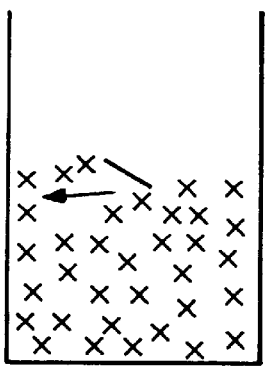
Figure 2C:
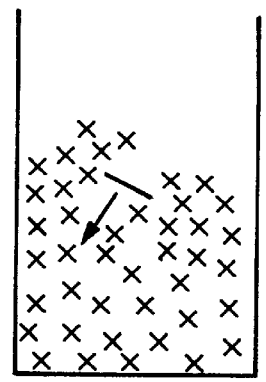
Figure 2D:
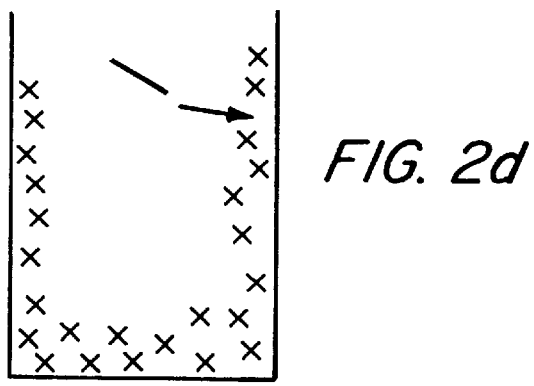

United States Patent [19]
Freeman et al.

[11] Patent Number: 6,065,330
[45] Date of Patent: May 23, 2000

[54] RHEOMETER WITH ANGLED BLADES

[76] Inventors: Reginald Edward Freeman, Boulters Farm, Castlemorton Common, Welland, Malvern, Worcestershire WR13 6LE; Christopher Martin Iles, 34 Southbourne Drive, Bourne End, Buckinghamshire SL8 5RZ, both of United Kingdom

[21] Appl. No.: 09/142,575

[22] PCT Filed: Mar. 24, 1997

[86] PCT No.: PCT/GB97/00806

§ 371 Date: Sep. 10, 1998

§ 102(e) Date: Sep. 10, 1998

[87] PCT Pub. No.: WO97/36162

PCT Pub. Date: Oct. 2, 1997

[30] Foreign Application Priority Data

Mar. 26, 1996 [GB] United Kingdom ............... 9606337

[51] Int. Cl.[7] ............................................. G01N 11/14
[52] U.S. Cl. ............................................. 73/54.28
[58] Field of Search ........................... 73/54.28, 54.29, 73/54.31, 54.32, 54.33, 54.34, 54.35

[56] References Cited

U.S. PATENT DOCUMENTS

| | | |
|---|---|---|
| 3,935,729 | 2/1976 | McCarthy . |
| 4,148,214 | 4/1979 | Madsen ........................... 73/54.28 |
| 4,530,701 | 7/1985 | Koskan et al. . |
| 5,118,439 | 6/1992 | Urfer et al. . |
| 5,357,785 | 10/1994 | Hemmings et al. .................. 73/54.32 |
| 5,531,102 | 7/1996 | Brookfield et al. . |

FOREIGN PATENT DOCUMENTS

| | | |
|---|---|---|
| 2092308 | 8/1982 | United Kingdom . |
| WO9203719 | 8/1991 | WIPO . |
| WO9509353 | 4/1995 | WIPO . |

OTHER PUBLICATIONS

International Search Report Jul. 4, 1997.
European Search Report Jun. 25, 1998.
"Brookfield Synchro–Electric Viscometer", product brochure, Brookfield Engineering Laboratories, Jan. 1970.

Primary Examiner—Daniel S. Larkin
Attorney, Agent, or Firm—Ira S. Dorman

[57] ABSTRACT

A rheometer for assessing characteristics of materials includes a vessel for containment of a material to be assessed, and a rotor which is, in use, passed through the material contained in the vessel, the rotor being comprised of a plurality of blades disposed at an angle relative to the axis of the rotor shaft. The vessel and rotor are constructed and adapted for rotation relative to one another about an axis and also for relative movement in the axial direction, and least one transducer is provided for determining the rotational and (optionally) axial forces that result from the relative motions(s) of the rotor and the material in order to thereby assess the characteristics of the material.

13 Claims, 3 Drawing Sheets

RHEOMETER WITH ANGLED BLADES

The present invention is concerned with a rheometer for assessing characteristics, such as flow characteristics, of materials.

Rheometers are used in a wide variety of chemical and material processing industries including pharmaceuticals, food processing, agrochemicals, paint and pigment manufacture, paper manufacture, catalysts, ceramics and cosmetics for determining and comparing characteristics, such as flow characteristics, of materials such as powders, liquids and semi-solids such as pastes, gels, ointments and the like. These materials generally combine the properties of a viscous liquid and an elastic solid, that is they are visco-elastic. The response of such materials to mechanical force is important for their proper manufacture and use and as a result rheometry is an important tool in their development, production and quality control.

Viscometers and rheometers are well known for assessing the characteristics of liquids and some semi-solids. However, these known instruments have limitations and are not suitable for many kinds of semi-solid materials. In particular, they are not suited to assessing the characteristics of powders when or while being mixed with other materials such as solid or liquid binders, surfactants or air. Known twin rotor mixing machines have been modified to carry out this assessment and a number of "mixer torque rheometers" are available commercially. These apparatus employ complex rotors, have a poor volumetric efficiency and lack sensitivity and repeatability. The lack of sensitivity and repeatability are due to the dependence of these apparatus on material being squeezed between two rotor blades rotating at different speeds.

The torque transient associated with this squeezing is recorded and used to assess the flow characteristics of the material. However, the amount of material trapped between the rotor blades is not consistent and leads to variable results. Only the speed of the rotors can be varied so that there is limited scope for sensitively testing materials having widely different characteristics.

Some torque rheometers have rotors that do not overlap, and the torque required to rotate one of the counter-rotating shafts is used to characterise the material. However, this type of torque rheometer has poor sensitivity and requires significant amounts of material in order to complete a test.

The poor volumetric efficiency of the known apparatus can lead to a significant proportion of the material remaining unmixed and this is a further cause of variability in the results. Additionally, poor volumetric efficiency renders the apparatus unsuited for assessing small quantities of material which is an important requirement for drug formulation.

A further problem with known apparatus is the difficulty of cleaning the bowl and rotors after use. Cleaning is important to avoid cross-contamination and in some cases to ensure recovery of as much material as possible.

U.S. Pat. No. 5,118,439 describes a viscometer in conjunction with a helipath stand in which a rotating shearing spindle describes a helical path through a test sample.

GB-A-2 092 308 describes a paddle arrangement for measuring the workability of concrete. The paddle is rotated in the concrete and the torque required to turn the paddle when immersed in fresh concrete is measured.

U.S. Pat. No. 4,530,701 describes the use of a Brookfield viscometer with helipath attachment in which spindles in the form of wire tees traced out helical patterns through fresh, unsheared volumes of sample. WO-A-9203719 describes a rheometer in which a cylindrical spindle is rotated in a cylindrical sample chamber. U.S. Pat. No. 3,935,729 describes a coaxial cylinder rheometer in which a cylindrical rotor rotates within an outer cylinder which contains a material to be tested. The rotor is movable axially as well as rotationally. WO-A-9509353 describes a viscometer in which the rotor can be changed automatically.

It is therefore an object of the present invention to provide a rheometer which eliminates or at least ameliorates the above-identified problems.

According to the present invention there is provided a rheometer for assessing characteristics of materials, the rheometer comprising:

a vessel for containing a material, the characteristics of which are to be assessed;

means disposed in use within the vessel for passing through a material to be assessed; and the vessel and the means disposed therewith in being constructed and adapted so as to be simultaneously:
rotatable relative to each other about an axis, and
movable in the axial direction relative to each other, wherein means is provided for determining rotational forces as a result of said relative motion in order to assess the characteristics of material within the vessel and wherein the means disposed within the vessel comprises rotor means in the form of a plurality of blades extending substantially radially from a rotor shaft and disposed at an angle relative to the axis of the shaft.

The rheometer may include means for determining axial forces as a result of said relative motion in order to assess the characteristics of material within the vessel.

Suitable materials can include liquids, powders and semi-solid mixtures of liquids and powders. The materials may additionally include air and/or one or more other gases.

The rheometer can be employed with individual ingredients or formulations that have previously been mixed using other means, for example as part of a production process. The rheometer is also capable of mixing ingredients together.

Control and measurement may be effected both during mixing and testing.

The rheometer can be used as a free-standing instrument or can be incorporated as an on-line unit built into product production equipment.

An important aspect of the rheometer according to the present invention is that passage through the material of the means for passing through the material to be assessed during assessment of the flow characteristics of the material is steady state. This gives rise to high repeatability of test results both on a given rheometer according to the present invention and between different rheometers according to the present invention.

By "steady state" there is meant herein that the set of variables defining the passage through the material to be assessed are either constant or varying at a relatively slow rate. "Relatively slow" in the present case means that the rheometer is capable of establishing a desired flow pattern that can be maintained for sufficient time (for example, at least several seconds) for the characterising data to be collected. In contrast to this, known mixer type rheometers rely on collecting transient data where the patterns of flow are constantly changing in a complex manner.

The vessel and the means disposed therewith in may be rotatable relative to each other at variable speed.

The vessel may be cylindrical or tapered, for example with the relatively narrow region of the vessel at the lower end thereof. The vessel may be made of a transparent material. The vessel may be reciprocable in the axial direction and may be moved at variable speed if desired. The vessel may be mounted on a table, for example by means of a clamp.

Alternatively or additionally, the means disposed within the vessel may be reciprocable in the axial direction and may be moved at variable speed if desired.

The means disposed within the vessel may pass through the material to be assessed in a manner such as to displace, move or work the material within the vessel. The forces imposed on the material during this process may be controlled so as to avoid over-compaction of the material and/or modification of the characteristics of the material.

The blades may be of twisted form, for example the angle of twist may be in proportion to the radial dimension of the blade. The rotor means may be rotatable clockwise and anti-clockwise. If desired, the rheometer may include means for holding the rotor stationary.

The combined motion of the vessel and the rotor means may be such that the rotor means describes a predetermined path through the material, usually helical in form although other controlled paths, such as circular and variable pitch helical paths, are possible. The relative axial and rotational speeds may determine the helix angle, the amount of material displaced and the forces imparted to the material during relative movement.

The determining means may include means for determining rotational (and optionally axial) forces on the means for passing through the material and on the vessel. The determining means may include controlling means.

The means for determining axial forces may comprise a force transducer. The means for determining rotational forces may comprise a torque transducer. The difference between rotor torque and vessel torque may be determined where required by using two torque transducers. The energy input to the material is readily monitored or controlled or limited by reference to the relative speeds of the vessel and the means therewith in together with the axial and rotational forces.

The rheometer may be employed additionally to collect or compact material prior to assessment. Compaction may be limited to a predetermined level.

The rheometer may be employed additionally to mix constituents of the material prior to assessment. One or more constituents of the material may be added incrementally.

Figure 3A:
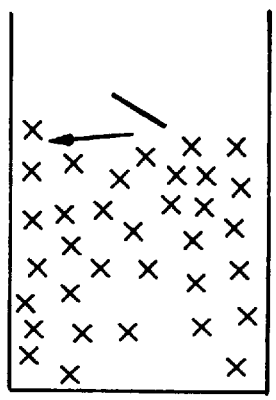
Figure 3B:
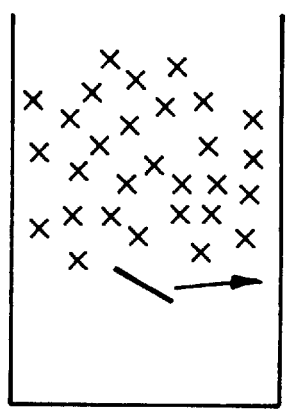
Figure 3C:
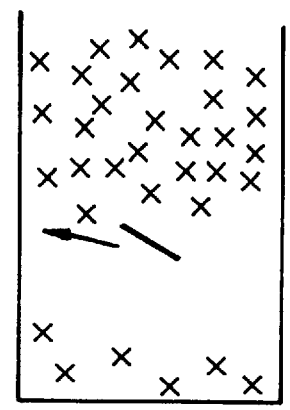
Figure 3D:
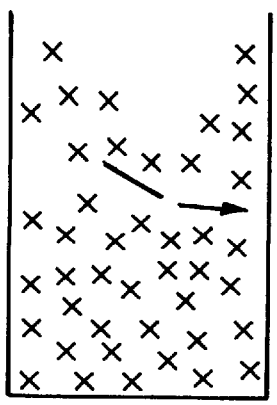
Figure 3E:
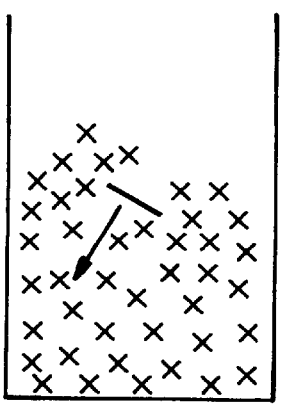
Figure 3F:
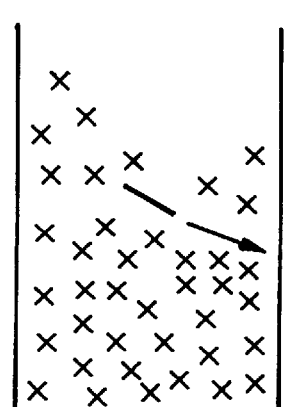
Figure 4:
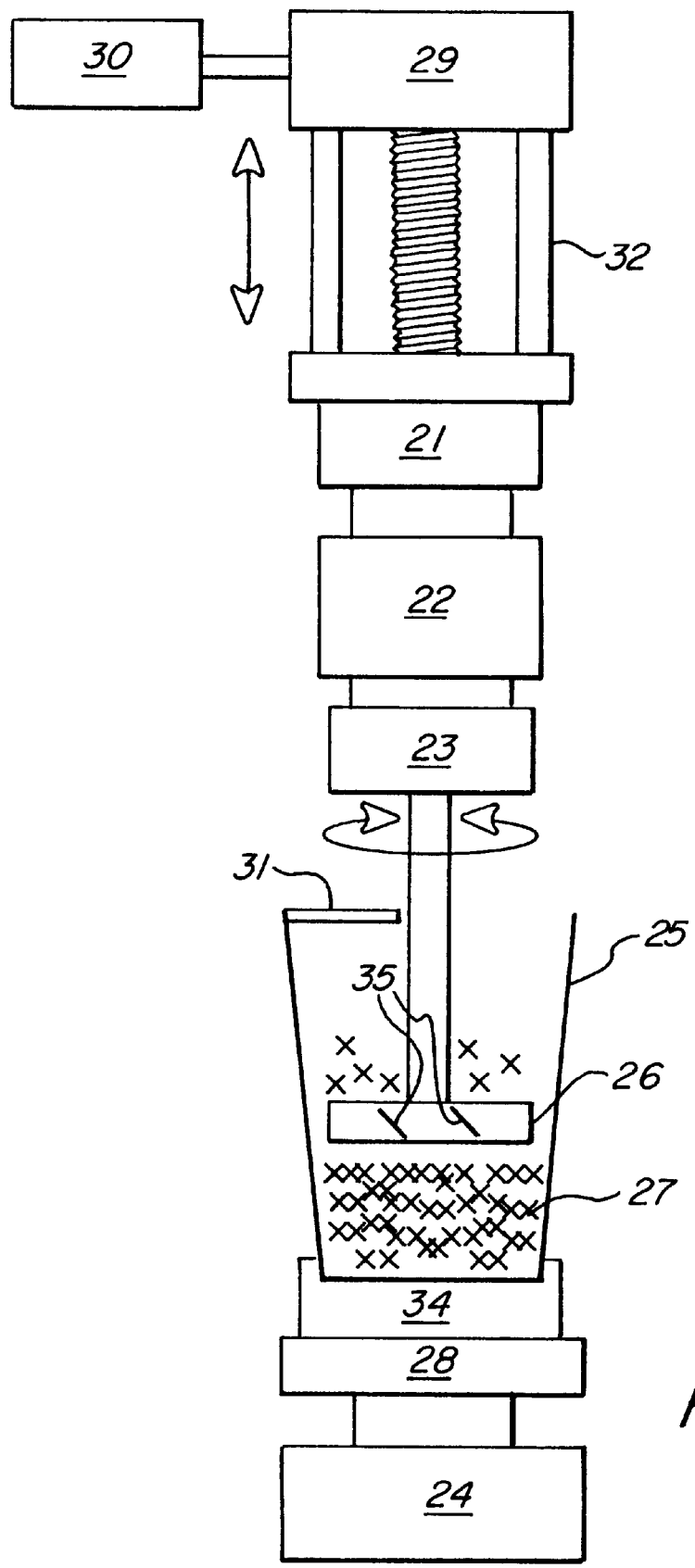

For a better understanding of the present invention and to show more clearly how it may be carried into effect reference will now be made, by way of example, to the accompanying drawings in which:

FIG. 1 is a diagrammatic illustration of one embodiment of a rheometer according to the present invention;

FIGS. 2(a)–(d) are a diagrammatic illustration of various assessment modes available with the rheometer according to the present invention;

FIGS. 3(a)–(f) are a diagrammatic illustration of various mixing modes available with the rheometer according to the present invention; and FIG. 4 is a diagrammatic illustration of another embodiment of a rheometer according to the present invention.

The rheometer shown in FIG. 1 comprises a generally cylindrical vessel 5 for containing a material 7 to be assessed and a rotor 6 provided with a pair of radial blades 15 which are angled relative to the axial direction and which are a close fit within at least a part of the vessel. The rotor 6 is substantially coaxial with the vessel 5 and may be held stationary or may be rotated at a variable speed either clockwise or anti-clockwise by a variable speed drive 1, such as a servo-motor, by way of a gearbox 2. The variable speed drive may be capable of functioning as part of a closed loop system so that predetermined levels or rates of change of force or torque may be achieved as will be described in more detail hereinafter. The vessel is provided with a scraper bar 11 in the region of the upper inner edge thereof to minimise any loss of material during use of the rheometer when the vessel is in the region of its fully lowered position. The vessel may be made of PYREX or similar transparent material to allow visual observation of the mixing and assessment process.

However, the vessel may be made of other materials or may take other forms if desired. For example, the vessel may be made of metal such as stainless steel and/or the vessel may be enclosed within a heating jacket for the preheating of material prior to and/or during assessment. The vessel may be closed at the upper end thereof if desired, the closure being provided with a suitable seal for the passage of the rotor shaft: such an arrangement allows collection of material at the top of the vessel followed by assessment in this position, allowing the material to be sheared and to fall to the bottom of the vessel under gravity such that sheared material cannot interfere with the remainder of the assessment procedure. The vessel may be tapered to provide variable clearance between the periphery of the rotor and the wall of the vessel: such an arrangement facilitates investigation of "powder packing" in which higher than normal resistance to flow is found when displacing material in close proximity to the wall of a containing vessel. Material exhibiting exothermic properties may be assessed in a vessel having suitable low thermal mass characteristics and a rotor shaft of low thermal conductivity. A temperature sensor may be provided to permit thermal characteristics to be studied. The relative isolation and simplicity of the vessel and rotor allow for the safe assessment of dangerous materials such as radioactive materials. A zone enclosing the vessel can be surrounded by appropriate screening and the assessment can be carried out automatically. Contaminated components, such as the vessel and possibly the rotor, can be disposed of, which is less practical with known mixer type apparatus.

The rotor assembly may be a single rotor having twin blades as illustrated, but alternatively the rotor assembly may incorporate twin rotors arranged coaxially such that each rotor may be held stationary or may be rotated in either direction irrespective of the direction of rotation of the other rotor so as to provide a wide range of differential rotor speeds. Twin blades may be provided as shown, for example of standard diameters adapted to different vessel diameters, but alternatively the or each rotor may have more that two blades, for example four, or special blade shapes may be employed.

The size of the rotor and the vessel may be selected to suit the amount of material to be assessed. For the pharmaceutical industry, the amount of material may range, for example, from 3 to 1000 grams. The ability to assess a small amount of material is especially important for the development of specialist drugs in the pharmaceutical industry.

The vessel 5 is supported on a reciprocating table 8 which can be raised or lowered in the axial direction of the vessel by means of a linear guidance system 12 the construction of which is well known to the skilled person, the vessel being secured to the table by a clamp 14. The table 8 is itself supported on a low friction bearing 13. The linear guidance system can be operated at a variable velocity by means of a variable speed reversible drive 10 and a gearbox 9.

The combined movements of the rotor and the vessel cause the rotor to move along a helical path through the material 7 contained within the vessel. The condition of least resistance to movement will occur when the helix angle is equal to the blade angle of the rotor. conversely, it is possible to achieve a combination of speeds of the rotor and the vessel such that the direction of movement of the blade through the material 7 is substantially perpendicular to the blade face. In this case, the resistance to movement will be a maximum and a maximum amount of material will be displaced. It will be clear that variation of the combination of speeds of the rotor and the vessel can additionally give rise to a complete range of controlled movement of the rotor blades relative to the material 7. Examples of operating modes will be described hereinafter with reference to FIGS. 2 and 3.

A force transducer 4 is provided to measure axial forces (compression and/or tension) imposed on the material 7 as it is displaced and a torque transducer 3 is provided to measure torque imposed on the material. The force transducer can be positioned to measure axial forces in the support for the table 8 as shown in FIG. 1 and/or in the shaft for driving the rotor 6. The torque transducer can be attached to the table 8 as shown in FIG. 1 and/or can measure the torque applied to the shaft for driving the rotor 6. The transducers 3 and 4 can additionally be used to prevent overload.

The rheometer is controlled by a computer (not shown) which monitors rotor force and torque and controls the speed of the rotor and table drives. Depending on the relative speeds and directions of the drives, various assessment modes are available, including:

(a) tests using predetermined combinations of rotor and table speeds;
(b) tests limited by predetermined force or torque settings; and
(c) constant shear stress testing whereby a fixed or programmed rate of change rotor torque or rotor force is maintained.

FIG. 2 shows various assessment modes with the arrow in each drawing indicating the direction of movement of the blade relative to the material within the vessel. FIG. 2(a) illustrates the situation where the helix angle is equal to the blade angle of the rotor (6), that is the condition of least resistance to movement of the blade and minimum displacement of the material. FIG. 2(b) illustrates an intermediate condition of moderate resistance to movement and moderate displacement of material. FIG. 2(c) illustrates the situation where the direction of movement of the blade is substantially perpendicular to the blade face, that is the condition of maximum resistance to movement of the blade and maximum displacement of the material. FIG. 2(d) illustrates the use of the apparatus to assess the forces required to shear the material adhering to the wall of the vessel.

The rheometer according to the present invention can be used in at least two different ways. In the case of powders and materials that have previously been prepared or mixed, the rheometer can be used to assess flow properties of the material by testing the material in one of the assessment modes described above. In order to ensure that the material is first suitably collected in the bottom of the vessel in preparation for testing, the rotor may be driven while the vessel is being raised in a direction to push the material in the opposite direction to the direction of movement of the vessel (FIG. 3(a)). The amount of compression or squeezing of the material when collected in this way can be limited by sensing the force and/or torque levels to ensure that a predetermined maximum is not exceeded. The limitation of force and/or torque levels is useful where it is important to avoid over-compaction of the material. For example, compression stresses may be limited by reference to processing and testing parameter information available to the controlling computer.

Some materials, however, will require a number of different constituents to be added to the vessel and mixed either prior to or during assessment of the flow characteristics of the material. The rheometer according to the present invention is capable of processing, or mixing the constituents of the material by utilising appropriate mixing modes. For example, a stiff, dough-like material may require to be chopped prior to being compressed, whereas a powder may need to be aerated and not compacted. FIG. 3 shows various mixing modes with the arrow in each drawing indicating the direction of movement of the blade relative to the material within the vessel. FIG. 3(a) illustrates the situation where the material is being collected in the bottom of the vessel in preparation for testing. FIG. 3(b) illustrates the converse of FIG. 3(a) in which the material is being collected at the top of the vessel. FIG. 3(c) illustrates slicing and downwards displacement of material collected at the top of the vessel. FIG. 3(d) illustrates a mixing mode in which material is sliced and projected against the wall of the vessel. FIG. 3(e) illustrates a mixing mode in which the movement of the blade through the material is substantially perpendicular to the blade face, that is maximum displacement of material. FIG. 3(f) illustrates a mixing mode in which the blade angle is substantially equal to the helix angle and the blade slices through the material with minimum disturbance.

Mixing and/or assessment conditions may also be determined by reference to information available to the controlling computer including, for example, details of test programmes. For example, a wet mix could be mixed and assessed while a binder (such as water) is incrementally or programmably added. A mixing and testing programme would then run until predetermined criteria are achieved.

Programmable binder addition may be effected, for example at a given volume per unit time, while the vessel is traversing downwardly or upwardly, or when the vessel is fully raised (i.e. the rotor is at the bottom of the vessel), and improves the distribution of the binder throughout the material and therefore affects the consistency of the material and the accuracy of the assessment. The binder may be added by injection into the vessel or by way of a rotor having a hollow shaft through which the binder can be pumped so as to be added to the material in the region of the rotor. In either case, binder addition can be incorporated into the processing and testing programme so as to be effected automatically.

In addition to, or as an alternative to, programmable binder addition, other constituents of the material may be added in an incremental or programmed manner. Such incremental or programmed additions give the option of mixing and assessing materials having varying proportions of constituents. As with binder addition, incremental or programmed additions of constituents can be effected automatically.

The amount of energy input to the material during the mixing and assessment stages can readily be calculated from the rotor speed and torque measurements and from the rotor force and vessel speed measurements. The variation of energy input as, for example, a function of time, revolutions of the rotor or excursions of the vessel can be displayed graphically if required.

The mixing and/or squeezing actions used are controllable so that the levels of shearing and compaction applied can be contained within predetermined limits.

We have found that the rheometer according to the present invention is well adapted for use in the following activities:

(a) Formulation, that is the formulation or development of new products involving a relatively small amount of material;
(b) Quality control applications, for example using small quantities of material to assess:
   b1) source variation in excipients and drugs;
   b2) batch variation in excipients and drugs;
   b3) binder type and concentration;
   b4) production monitoring;
(c) Establishing optimum processing conditions and the effect of processing variables such as mixing time;
(d) Scaling, that is deriving information from a small scale assessment for use in determining conditions appropriate for large scale manufacture.

The rheometer according to the present invention has high sensitivity and is capable of assessing characteristics, such as flow characteristics, of powders, liquids and semi-solids having a very wide range of viscosity. This sensitivity is achieved because the angle at which the blades of the rotor approach the material can be varied to suit the flow characteristics of the material itself. The flow forces acting on a blade when moving through a material, such as a powder, depends greatly on the angle of the blade with respect to the direction of movement. At right angles, the resistance to movement is very high and relative movement may not be possible, but when in line the blade will cut easily and experience little resistance. Assessment can therefore be carried out at whatever "angles of approach" are appropriate for any particular material.

With the blades being a close fit within the vessel, the unswept volume within the vessel is small. The result of this is that the mixing efficiency of the rheometer is high in comparison with known apparatus.

The rheometer shown in FIG. 4 is similar to that shown in FIG. 1, the most significant difference being that relative axial movement is effected by movement of the rotor rather than the vessel.

The rheometer shown in FIG. 4 comprises a generally tapered vessel 25 for containing a material 27 to be assessed and a rotor 26 provided with a pair of radial blades 35 which are angled relative to the axial direction and which are a close fit within at least a part of the vessel. The rotor 26 is substantially coaxial with the vessel 25 and may be held stationary or may be rotated at a variable speed either clockwise or anti-clockwise by a variable speed drive 21, such as a servo-motor, by way of a gearbox 22. As with the embodiment of FIG. 1, the variable speed drive may be capable of functioning as part of a closed loop so that predetermined levels or rates of change of force or torque may be achieved. The vessel is provided with a scraper bar 31 in the region of the upper inner edge thereof to minimise any loss of material during use of the rheometer when the rotor is in the region of its fully raised operational position.

The form of the rotor blade and of the vessel may be substantially the same as those described above in respect of FIG. 1.

The rotor 26 can be raised and lowered in the axial direction by means of a linear guidance system 32 the construction of which is well known to the skilled person. The liner guidance system 32 can be operated at a predetermined variable velocity by means of a variable speed reversible drive 30 and a gearbox 29.

A torque transducer 23 is provided to measure torque imposed on the material 27. The torque transducer can be applied to the shaft for driving the rotor 26 as shown in FIG. 4 and/or can be attached to the table 28.

The vessel 25 is secured to a table 28 by means of a clamp 34, a force transducer 24 being provided to measure axial forces (compression and/or tension) imposed on the material 27 as it is displaced. The force transducer 24 can be positioned to measure axial forces in the support for the table 28 as shown in FIG. 4 and/or in the shaft for driving the rotor 26.

Operation of the rheometer shown in FIG. 4 is essentially the same as that shown in FIG. 1.

An important aspect of the rheometer according to the present invention is that the shear flow (or compression) phase set up during assessment of the flow characteristics of the material is steady state. This is in direct contrast to known apparatus based on conventional mixers which rely on a transient torque peak. The steady state flow mode as the rotor follows a helical path allows the shear flow (or compression) phase to be maintained in a manner that is readily quantifiable in terms of force and torque measurements and amenable to theoretical analysis. Additionally, the steady state flow mode allows the variability of the material to be assessed as the vessel is raised and the total volume of the material is displaced. The rheometer according to the present invention is therefore sensitive to non-homogeneity of the material whether this arises as a result of inadequate mixing or due to other factors.

We claim:

1. A rheometer for assessing characteristics of materials, the rheometer comprising:
   a vessel (5, 25) for containing a material (7, 27), the characteristics of which are to be assessed;
   means (6, 26) disposed in use within the vessel for passing through a material to be assessed; and
   the vessel (5, 25) and the means (6, 26) disposed therewith in being constructed and adapted so as to be simultaneously:
      rotatable relative to each other about an axis, and
      movable in the axial direction relative to each other,
   wherein means (3, 23) is provided for determining rotational forces as a result of said relative motion in order to assess the characteristics of material (7, 27) within the vessel (5, 25) and wherein the means (6, 26) disposed within the vessel comprises rotor means in the form of a plurality of blades extending substantially radially from a rotor shaft and disposed at an angle relative to the axis of the shaft.

2. A rheometer as claimed in claim 1, wherein means (4, 24) is provided for determining axial forces as a result of said relative motion in order to assess the characteristics of material (7, 27) within the vessel (5, 25).

3. A rheometer as claimed in claim 1, wherein the vessel (5, 25) and the means (6, 26) disposed therewith in are rotatable relative to each other at variable speed.

4. A rheometer as claimed in claim 1, wherein the vessel (5, 25) is cylindrical.

5. A rheometer as claimed in claim 1, wherein the vessel (5, 25) is tapered.

6. A rheometer as claimed in claim 5, wherein the vessel (5, 25) is tapered with a relatively narrow region of the vessel at a lower end thereof.

7. A rheometer as claimed in claim 1, wherein the vessel (5, 25) is reciprocable in the axial direction thereof.

8. A rheometer as claimed in claim 7, wherein the vessel (5, 25) is movable at variable speed.

9. A rheometer as claimed in claim 1, wherein the means (6, 26) disposed within the vessel is reciprocable in the axial direction thereof.

10. A rheometer as claimed in claim 9, wherein the means (6, 26) disposed within the vessel is movable at variable speed.

11. A rheometer as claimed in claim 1, wherein the blades are of twisted form.

12. A rheometer as claimed in claim 11, wherein the angle of twist is in proportion to the radial dimension of the blade.

13. A rheometer as claimed in claim 1 and including means for holding the rotor stationary.

* * * * *